United States Patent [19]

Yamaguchi et al.

[11] Patent Number: 4,987,261
[45] Date of Patent: Jan. 22, 1991

[54] DIAMINOINDANE DERIVATIVES

[75] Inventors: Keizaburo Yamaguchi, Chiba; Masayuki Ooe, Yokohama; Akihiro Yamaguchi, Kamakura, all of Japan

[73] Assignee: Mitsui Toatsu Chemicals, Inc., Tokyo, Japan

[21] Appl. No.: 393,797

[22] Filed: Aug. 15, 1989

[51] Int. Cl.$^5$ ............................................. C07C 211/04
[52] U.S. Cl. ..................................................... 564/428
[58] Field of Search .......................................... 564/428

[56] References Cited

U.S. PATENT DOCUMENTS

| | | | |
|---|---|---|---|
| 3,393,995 | 7/1968 | Evans et al. | 564/428 X |
| 4,340,758 | 7/1982 | Lapporte et al. | 564/419 X |
| 4,433,169 | 2/1984 | Scholl | 564/419 |

OTHER PUBLICATIONS

Wagner et al., "Synthetic Organic Chemistry", ppp. 746–749 (1963).

*Primary Examiner*—Robert V. Hines
*Attorney, Agent, or Firm*—Burns, Doane, Swecker & Mathis

[57] ABSTRACT

The invention relates to diaminoindane derivatives represented by the following formula:

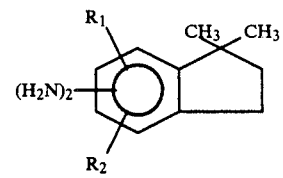

wherein $R_1$ and $R_2$ are each selected from the group consisting of a hydrogen atom and a lower alkyl group having from 1 to 4 carbon atoms, and a process for preparing same.

7 Claims, 2 Drawing Sheets

DIAMINOINDANE DERIVATIVES

BACKGROUND OF THE INVENTION (i) Field of the Invention

The present invention relates to novel diaminoindane derivatives and a process for the preparation thereof. The diaminoindane derivatives of the invention are useful as raw materials for isocyanates, epoxy resins, bismaleimides and the like and also as curing agents for isocyanates, for example, RIM urethanes. The diaminoindane derivatives can also be used as curing agents for epoxy resins and bismaleimides and can be added as modifiers to various resins, rubbers and the like.

(ii) Description of the Related Art

Diamine compounds which have been used for the above-described applications prior to the present invention include bis(4-aminophenyl)methane; 2,4-diamino-3,5-diethyltoluene and 2,6-diamino-3,5-diethyltoluene (hereinafter "DETDA" collectively); 2,4-diamino-5-tert-butyltoluene and 2,6-diamino-3-tert-butyltoluene (hereinafter "t-BTDA" collectively).

Bis(4-aminophenyl)methane (hereinafter "MDA") has been prepared by the condensation of aniline with formaldehyde.

As disclosed in U.S. Pat. No. 4,219,502 and European Patent No. 177,916 DETDA and t-BTDA have been prepared by ethylating or tert-butylating 2,4-diaminotoulene or 2,6-diaminotoluene.

The above diamines have both benefits and disadvantages in handling, properties and preparation. For example, bis(4-aminophenyl)methane is economical but has disadvantages such as a high melting point and does not form a homogeneous mixture. It is accompanied by a further drawback that it is unstable to heat, light and oxygen in air, and when employed as a curing agent, the curing reaction proceeds too quickly.

On the other hand, DETDA and t-BTDA which have been prepared by alkylation of diaminotoluenes are generally in a liquid form and enjoy easy handling. Their use as curing agents for RIM urethanes is however accompanied by the drawback that curing proceeds too quickly with DETDA and too slowly with t-BTDA.

SUMMARY OF THE INVENTION

The present invention overcomes the problems and disadvantages of the prior art by providing diaminoindane derivatives useful as raw materials for isocyanates, epoxy resins, bismaleimides and the like and as curing agents for urethanes.

It is an object of this invention to provide novel diaminoindane derivatives having a suitable degree of reactivity and are useful as curing agents for RIM urethanes.

It is a further object of this invention to provide a process for preparing these novel compounds.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein, the invention comprises diaminoindane derivatives represented by the following formula (I):

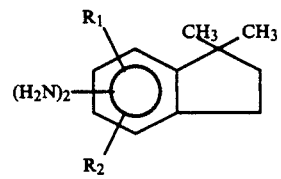

wherein $R_1$ and $R_2$ each represent a hydrogen atom or a lower alkyl group having from 1 to 4 carbon atoms.

The present invention also provides a process for the preparing of the diaminoindane derivatives of the formula (I), comprising dinitrating an indane derivative represented by the following formula (II):

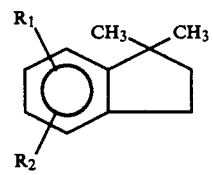

wherein $R_1$ and $R_2$ have the same meanings as defined above with respect to the formula (I), and then reducting the dinitrated indane derivative.

The diaminoindane derivatives of the invention exhibit a more suitable curing velocity than conventional diamines, particularly when employed as curing agents for RIM urethanes. The diaminoindane derivatives exhibit a degree of reactivity which falls between the reactivities of DETDA and t-BTDA. The diaminoindane derivatives exhibit improved workability and cured articles prepared therefrom have significantly improved properties.

The diaminoindane derivatives of this invention are useful in numerous applications in addition to being useful as curing agents. Furthermore, these compounds may be prepared economically by the process of the invention.

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
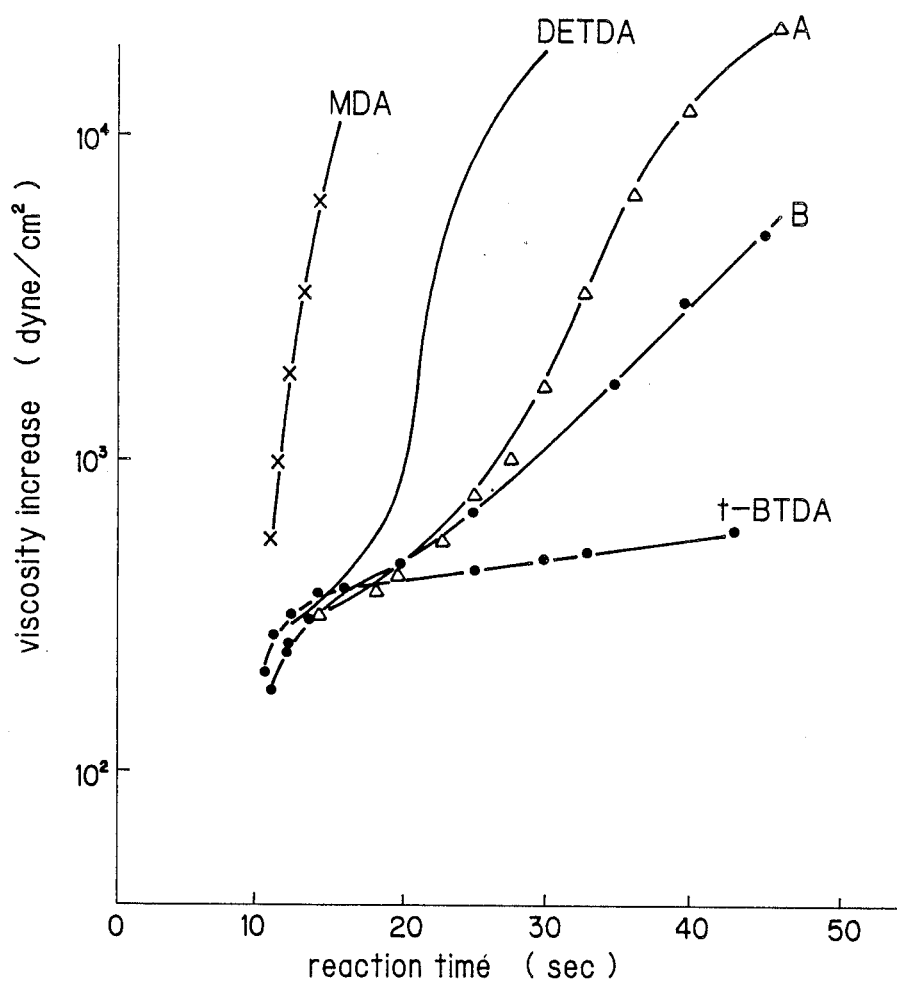
FIG. 1 shows viscosity increase curves of urethanes in which various diamines were employed as curing agents. Letters A and B represent a diaminoindane derivative obtained in Example 1, and a diaminoindane derivative obtained in Example 3, respectively.
Figure 2:
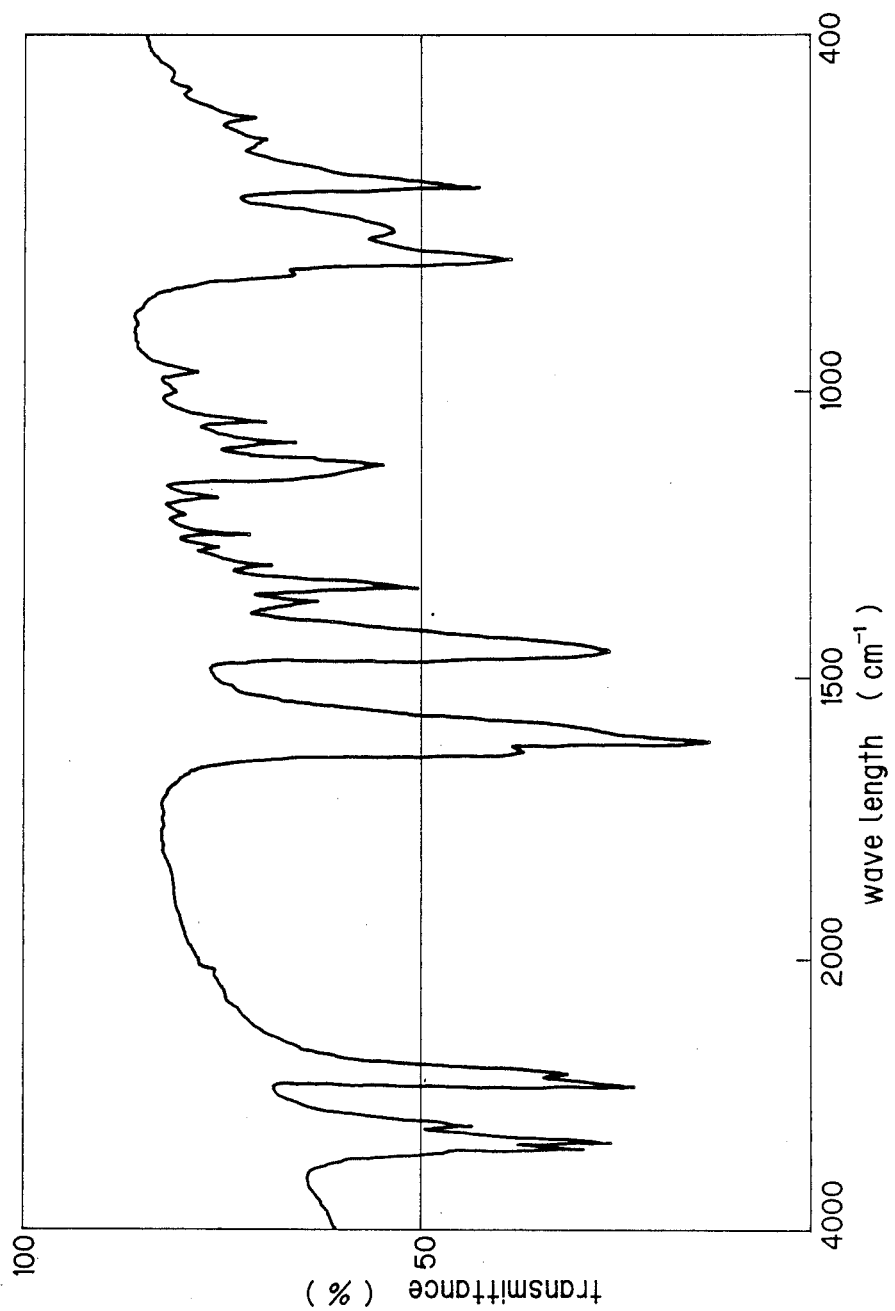
FIG. 2 is an IR spectrum (KBr) diagram of the diaminoindane derivative obtained in Example 1.

Reference will now be made in detail to the preferred embodiments of applicants' invention.

The diaminoindane derivatives of this invention are represented the formula (I) and include the following exemplary compounds:

5,7-Diamino-1,1-dimethylindane;
4,6-Diamino-1,1-dimethylindane;
4,7-Diamino-1,1-dimethylindane;

5,7-Diamino-1,1,4-trimethylindane;
5,7-Diamino-1,1,6-trimethylindane;
5,7-Diamino-1,1-dimethyl-4-ethylindane;
5,7-Diamino-1,1-dimethyl-6-ethylindane;
5,7-Diamino-1,1-dimethyl-4-isopropylindane;
5,7-Diamino-1,1-dimethyl-6-isopropylindane;
5,7-Diamino-1,1-dimethyl-4-n-propylindane;
5,7-Diamino-1,1-dimethyl-6-n-propylindane;
5,7-Diamino-1,1-dimethyl-4-sec-butylindane;
5,7-Diamino-1,1-dimethyl-6-sec-butylindane;
5,7-Diamino-1,1-dimethyl-4-n-butylindane;
5,7-Diamino-1,1-dimethyl-6-n-butylindane;
5,7-Diamino-1,1-dimethyl-4-tert-butylindane;
5,7-Diamino-1,1-dimethyl-6-tert-butylindane;
5,7-Diamino-1,1,4,6-tetramethylindane;
6,7-Diamino-1,1,4,5-tetramethylindane;
5,6-Diamino-1,1,4,7-tetramethylindane;
4,7-Diamino-1,1,5,6-tetramethylindane;
5,7-Diamino-1,1-dimethyl-4,6-diethylindane;
5,7-Diamino-1,1-dimethyl-4,6-diisopropylindane; and
5,7-Diamino-1,1,4-trimethyl-6-tert-butylindane;

The diaminoindane derivatives of this invention can be prepared by dinitrating indane derivatives and then reducing the dinitrated intermediates.

Indane derivatives useful as raw materials in the process of this invention can be prepared by reacting corresponding benzene derivatives with isoprene in the presence of an acid catalyst [P.W.K. Flanagan, et al.: The Journal of Organic Chemistry, 33(5), 2000–2008 (1968)].

Exemplary suitable indane derivatives for use in the process of the invention include
1,1-Dimethylindane;
1,1,4-Trimethylindane;
1,1,6-Trimethylindane;
1,1-Dimethyl-4-ethylindane;
1,1-Dimethyl-6-ethylindane;
1,1-Dimethyl-4-isopropylindane;
1,1-Dimethyl-6-isopropylindane;
1,1-Dimethyl-4-n-propylindane;
1,1-Dimethyl-6-n-propylindane;
1,1-Dimethyl-4-sec-butylindane;
1,1-Dimethyl-6-sec-butylindane;
1,1-Dimethyl-4-n-butylindane;
1,1-Dimethyl-6-n-butylindane;
1,1-Dimethyl-4-tert-butylindane;
1,1-Dimethyl-6-tert-butylindane;
1,1,4,6-Tetramethylindane;
1,1,4,5-Tetramethylindane;
1,1,5,6-Tetramethylindane;
1,1,4,7-Tetramethylindane;
1,1,6,7-Tetramethylindane;
1,1-Dimethyl-4,6-diethylindane; and
1,1,4-TrimethYl-6-tert-butylindane.

A mixture of isomers formed from the reaction between a benzene derivative and isoprene is used in many industrial applications.

To prepare dinitroindane derivatives as intermediates from these raw materials, the raw materials are dinitrated with a conventional nitrating agent. A mixed acid, fuming nitric acid, nitric acid-acetic acid or any other suitable known nitrating agent can be used as the nitrating agent. Mixed acid or fuming nitric acid is preferably employed. When fuming nitric acid is used as a nitrating agent, 80–98% nitric acid may be used in a molar amount of from about 3 to about 12 times the indane derivative. When a mixed acid is used, it may be formed of a combination of nitric acid or a nitrate such as sodium nitrate or potassium nitrate and concentrated sulfuric acid. The indane derivative, nitric acid or a nitrate and concentrated sulfuric acid may be used in a molar ratio of from about 2.2 to about 5 mole of nitric acid or nitrate and from about 1 to about 5 mole of concentrated sulfuric acid per mole of indane derivative.

The dinitration reaction may be conducted in a reaction solvent as needed. Suitable exemplary reaction solvents include halogenated hydrocarbon solvents such as methylene chloride, 1,2-dichloroethane, 1,1,2-trichloroethane, chloroform, carbon tetrachloride, 1,1,2,2-tetrachloroethane and trichloroethylene.

The reaction temperature may be about 5° C. or lower, preferably in from about $-30°$ C. to about 5° C. more preferably in a range of from about $-20°$ C. to about 0° C.

If the reaction temperature is too low, the dinitration proceeds slowly and it is difficult to bring the dinitration to completion. On the other hand, unduly high reaction temperatures result in an extreme increase of byproducts, for example, due to oxidation of the methylene groups of the indane derivative, thereby leading to a lowered yield. Such unduly low or high temperatures are hence not preferred.

Dinitration at a temperature of about 5° C. or lower inhibits side reactions, whereby the diaminoindane derivatives of the invention can be prepared in a high yield.

The dinitration reaction can be effected by any suitable method, for example, by adding the indane derivative dropwise into the nitrating agent or by adding the nitrating agent dropwise into the indane derivative. When a mixed acid is used, the nitration reaction can be conducted, for example, by using the mixed acid prepared in advance or by mixing the raw material with one of the acids and then adding the other acid into the mixture.

After completion of the reaction, the reaction mixture is diluted with ice water to separate a powdery or oily substance. The substance is collected by filtration or is extracted with a solvent and then concentrated, whereby the dinitroindane derivative is obtained as an intermediate. When the dinitration reaction is conducted using a solvent, the reaction mixture separates into two layers provided that the reaction mixture is diluted with water after the reaction. It is hence only necessary to separate and concentrate the oil layer.

The dinitroindane derivative obtained by the above dinitration reaction is then reduced to obtain the corresponding diaminoindane derivatives of the invention.

No particular limitation is imposed on the method for reducing the dinitroindane derivative. Various methods adapted to reduce nitro groups into amino groups may be employed. Catalytic reduction is however most preferred from the industrial viewpoint.

Exemplary reducing catalysts suitable for the catalytic reduction include metal catalysts employed routinely for catalytic reduction, for example, nickel, palladium, platinum, rhodium, ruthenium, cobalt, copper, and the like. Use of a palladium catalyst is preferred from the industrial viewpoint.

These catalysts may be used in a metal form. However, they are usually employed in a form carried on the surface of a carrier such as carbon, barium sulfate, silica gel, alumina or celite or as Raney catalysts with nickel, cobalt, copper or the like.

No particular limitation is imposed on the amount of the catalyst to be used. It is preferable that the catalyst be employed in an amount of from about 0.01% to about 10% metal by weight based on the weight of the intermediate dinitroindane derivative. More preferably, when used in a metal form, the catalyst is employed in an amount of from about 2% to about 8% by weight, and in an amount of from about 0.1% to about 5% by weight when borne on a carrier.

No particular limitation is imposed on the reaction solvent providing that the solvent is inert to the reaction. Exemplary suitable solvents include alcohols such as methanol, ethanol and isopropyl alcohol; glycols such as ethylene glycol and propylene glycol; ethers such as ethyl ether, dioxane, tetrahydrofuran and methylcellosolve; aliphatic hydrocarbons such as hexane and cyclohexane; aromatic hydrocarbons such as benzene, toluene and xylene; esters such as ethyl acetate and butyl acetate; halogenated hydrocarbons such as dichloromethane, chloroform, carbon tetrachloride, 1,2-dichloroethane, 1,1,2-trichloroethane and tetrachloroethane; and N,N-dimethylformamide. Alcohols, glycols and ethers may also be employed. When a reaction solvent which is immiscible with water is used, and the reaction velocity is slow, the reaction can be caused to proceed faster by adding a conventional phase transfer catalyst such as a quaternary ammonium salt or quaternary phosphonium salt.

The solvent is employed in an amount sufficient to suspend the intermediate or completely dissolve the same. Preferably, the solvent is employed in an amount from about 0.5 to about 10 times by weight of the intermediate.

Generally, the reaction is carried out at a temperature of from about 20° C to about 200° C, preferably from about 20° C to about 100° C. The reaction pressure is generally from about normal pressure to about 150 atm.

The catalytic reduction is generally conducted by adding the catalyst to a solution or suspension of the intermediate and then introducing hydrogen under stirring at a prescribed temperature. The end of the reaction can be determined from the amount of hydrogen absorbed or by means of thin-layer chromatography or high-performance liquid chromatography.

After completion of the reaction, the target product can be obtained by removing the catalyst and the like employed for the reduction, concentrating the filtrate and then allowing it to deposit as crystals. As an alternative, the target compound can also be isolated by distilling the filtrate.

The diaminoindane derivatives prepared in accordance with the process of this invention are often obtained as mixtures of isomers depending on the type of indane derivatives employed as raw material. Diaminoindane compounds derived respectively from an unsubstituted 1,1-dimethylindane, mono-substituted derivatives of 1,1-dimethylindane and a di-substituted derivative of 1,1-dimethylindane in accordance with the process of this invention were fractionated by silica gel column chromatography and their chemical structures were identified by NMR analysis. The following results were obtained.

From unsubstituted 1,1-dimethylindane, a composition was obtained containing a small amount of 4,7-diamino-1,1-dimethylindane in addition to 4,6-diamino-1,1-dimethylindane and 5,7-diamino-1,1-dimethylindane. The yields of orthodiamine compounds were very small and thus were ignorable.

One to three isomers were formed from a monosubstituted 1,1-dimethylindane. From 1,1,4-trimethylindane, 5,7-diamino-1,1,4-trimethylindane was obtained. Orthodiamine compounds were observed only in extremely trace concentrations. From 1,1,6-trimethylindane, a composition consisting of 5,7-diamino-1,1,6-trimethylindane, 4,7-diamino-1,1,6-trimetylindane and 4,5-diamino-1,1,6-trimethylindane was obtained.

Only one diamine compound was obtained from a di-substituted 1,1-dimethylindane. From 1,1,4,6-tetramethylindane, 5,7-diamino-1,1,4,6-tetramethylindane was obtained.

This invention will be further clarified by the following examples, which are intended to be purely exemplary of the invention. Example 1

A reaction flask fitted with a stirrer, a thermometer and a condenser was charged with 300 g (2.82 mol) of m-xylene. The content was cooled to −15° C, to which 165 g (1.56 mol) of 93% sulfuric acid was added dropwise. A mixture of 68 g (1.00 mol) of isoprene and 150 g (1.41 mol) of m-xylene was then added dropwise over 7 hours while maintaining the reaction temperature around −10° C. The resultant mixture was stirred for additional 1 hour at the same temperature. After completion of the reaction, the reaction mixture was left over and the resulting sulfuric acid layer was removed. The organic layer was added with 300 g of 20% saline, followed by neutralization with aqueous ammonia. The mixture was heated to 70–80° C. and the resulting water layer was removed. Excess m-xylene was distilled off under reduced pressure. The thus-obtained residue was distilled under reduced pressure to obtain 1,1,4,6-tetramethylindane as a colorless liquid.

Yield: 120 g (69%).
Boiling point: 105–106° C. (16 mmHg).
$^1$H-NMR (CDCl$_3$,TMS) δppm:
1.25 (6H, s, 1-Me ×2),
1.90 (2H, t, 2-CH$_2$),
2.21 (3H, s, 4-Me or 6-Me),
2.31 (3H, s, 4-Me or 6-Me),
2.72 (2H, t, 3-CH$_2$),
6.77 (2H, s, 5-H and 7-H).

One hundred twenty grams (0.688 mol) of the 1,1,4,6-tetramethylindane thus obtained were added dropwise to a mixture of 101 g (1.5 mol) of nitric acid having a specific gravity of 1.52, 417 g (4.17 mol) of 98% sulfuric acid and 300 g of 1,2-dichloroethane, which had been cooled to −5° C. in advance, over 2 hours while maintaining the reaction temperature within a range of from −5° C to 0° C. After the addition, the contents were stirred for additional 1 hour at the same temperature. After completion of the reaction, 400 g of water were added to the reaction mixture under cooling to dilute the sulfuric layer. The resultant mixture was allowed to stand to form an organic layer. The organic layer was separated and then 500 g of water were added. 1,2-Dichloroethane was distilled off as an azeotropic mixture. Deposited crystals were collected by filtration, washed with water and then dried to obtain 5,7-dinitro-1,1,4,6-tetramethylindane as pale yellow crystals.

Yield: 175 g (96%).
Melting point: 91–93° C. $^1$H-NMR (CDC$_3$ , TMS) δppm:
1.38 (6H, s, 1-Me×2),
2.08 (2H, t, 2-CH$_2$),
2.20 (3H, s, 4-Me or 6-Me),
2.28 (3H, s, 4-Me or 6-Me),
2.87 (2H, t, 3-CH$_2$).
Elemental analysis:

|  | C | H | N |
|---|---|---|---|
| Calculated (%): | 59.09 | 6.10 | 10.60 |
| Found (%): | 59.03 | 5.86 | 10.52 |

One hundred seventy-five grams (0.662 mol) of the 5,7-dinitro-1,1,4,6-tetramethylindane thus obtained were dissolved in 500 g of methanol, and after addition of 17.5 g of 5% Pd/C (water content: 50%) to the resultant solution, the mixture was stirred at 50–60° C. for 84 hours in a hydrogen gas atmosphere. After completion of the reaction, the reaction mixture was filtered and the filtrate was concentrated under reduced pressure. The thus-obtained residue was distilled under reduced pressure to obtain 5,7-diamino-1,1,4,6-tetramethylindane as pale yellow crystals.

Yield: 124 g (92.1%).
Melting point: 77–78.5° C.
Boiling point: 148–150° C. (3 mmHg).
$^1$H-NMR (CDCl$_3$, TMS) δppm:
1.38 (6H, s, 1-Me×2),
1.86 (2H, t, 2-CH$_2$),
1.99 (3H, s, 4-Me or 6-Me),
2.03 (3H, s, 4-Me or 6-Me),
2.73 (2H, t, 3-CH$_2$),
3.3–3.5 (4H, br. s, NH$_2$×2).
Elemental analysis:

|  | C | H | N |
|---|---|---|---|
| Calculated (%): | 76.42 | 9.87 | 13.71 |
| Found (%): | 75.61 | 10.25 | 13.95 |

EXAMPLES 2–4

From benzene, toluene and isopropylbenzene, the corresponding indane compounds were prepared, respectively. They were separately dinitrated and reduced in a similar manner to Example 1, whereby diamines having the diamine skeletons shown respectively in Table 1 were obtained.

parts of a solution. The solution was then added with 0.01 g of dibutyltin dilaurate and further with 12.1 g of an isocyanate which was a prepolymer obtained by reacting a mixture of diphenyl methanediisocyanate and a carbodiimidomodified derivative thereof with tripropylene glycol and having a NCO content of 26%. The resultant mixture was then stirred.

As an index representing the reactivity, the viscosity increase (loss modulus) was measured by a "RHEOMETER" (manufactured by Toyo Seiki Seisaku-Sho, Ltd.) immediately after conducting the above stirring for 5 seconds.

The results are diagrammatically depicted in FIG. 1.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A diaminoindane derivative of the formula (I):

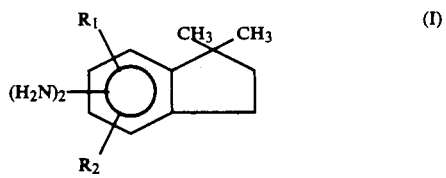

wherein R$_1$ and R$_2$ are each selected from the group consisting of a hydrogen atom and a lower alkyl group having from 1 to 4 carbon atoms.

2. The diaminoindane derivative of claim 1 wherein the derivative is selected from
5,7-diamino-1,1-dimethylindane;
4,6-diamino-1,1-dimethylindane;
4,7-diamino-1,1-dimethylindane;
5,7-diamino-1,1,4 -trimethylindane;
5,7-diamino-1,1,6 -trimethylindane;
5,7-diamino-1,1-dimethyl-4-ethylindane;

TABLE 1

| Ex. | Indane compound Composition Compound | Molar ratio | Yield[1] (%) | Diaminoindane Composition[2] Compound | Ratio | m.p. (°C.) | b.p. (°C.) |
|---|---|---|---|---|---|---|---|
| 2 | 1,1-Dimethylindane | 10 | 92.0 | 4,6-Diamino-1,1-dimethylindane | 47.8 | 80–89 | 127–130/ (1 mmHg) |
|  |  |  |  | 4,7-Diamino-1,1-dimethylindane | 14.5 |  |  |
|  |  |  |  | 5,7-Diamino-1,1-dimethylindane | 37.7 |  |  |
| 3 | 6-Methyl-1,1-dimethylindane | 7 | 94.6 | 4,7-Diamino-1,1,6-trimethylindane | 16.5 | 60–77 | 147.5–150/ (4 mmHg) |
|  | 4-Methyl-1,1-dimethylindane | 3 |  | 5,7-Diamino-1,1,6-trimethylindane | 48.6 |  |  |
|  |  |  |  | 4,5-Diamino-1,1,6-trimethylindane | 9.2 |  |  |
|  |  |  |  | 5,7-Diamino-1,1,4-trimethylindane | 25.7 |  |  |
| 4 | 6-Isopropyl-1,1-dimethylindane | 9 | 94.5 | 4,7-Diamino-6-isopropyl-1,1-dimethylindane | 8.9 | 81–91 | 158–161/ (5 mmHg) |
|  | 4-Isopropyl-1,1-dimethylindane | 1 |  | 5,7-Diamino-6-isopropyl-1,1-dimethylindane | 75.8 |  |  |
|  |  |  |  | 4,5-Diamino-6-isopropyl-1,1-dimethylindane | 18.7 |  |  |
|  |  |  |  | 5,7-Diamino-4-isopropyl-1,1-dimethylindane | 13.4 |  |  |

[1]Yield based on the starting indane compound.
[2]The composition is determined by means of H[1]-NMR and high-performance liquid chromatography.
[3]The ratio is the area determined by means of high-performance liquid chromatography.

Application Example

Using the diamines obtained in Examples 1 and 3, respectively and commercially-available 4,4'-diaminodiphenylmethane, DETDA and t-BTDA, their reactivities as curing agents for urethanes were compared. Namely, 0.025 mol of each diamine compound was dissolved in dioxypropylene glycol to give 100

5,7-diamino-1,1-dimethyl-6-ethylindane;
5,7-diamino-1,1-dimethyl-4-isopropylindane;
5,7-diamino-1,1-dimethyl-6-isopropylindane;
5,7-diamino-1,1-dimethyl-4-n-propylindane;
5,7-diamino-1,1-dimethyl-6-n-propylindane;
5,7-diamino-1,1-dimethyl-4-sec-butylindane;
5,7-diamino-1,1-dimethyl-6-sec-butylindane;

5,7-diamino-1,1-dimethyl-4-n-butylindane;
5,7-diamino-1,1-dimethyl-6-n-butylindane;
5,7-diamino-1,1-dimethyl-4-tert-butylindane;
5,7-diamino-1,1-dimethyl-6-tert-butylindane;
5,7-diamino-1,1,4,6-tetramethylindane;
6,7-diamino-1,1,4,5-tetramethylindane;
5,6-diamino-1,1,4,7-tetramethylindane;
4,7-diamino-1,1,5,6-tetramethylindane;
5,7-diamino-1,1-dimethyl-4,6-diethylindane;
5,7-diamino-1,1-dimethyl-4,6-diisopropylindane; and
5,7-diamino-1,1,4-trimethyl-6-tert-butylindane.

3. The diaminoindane derivative of claim 12 wherein the derivative is 5,7-diamino-1,1,4,6-tetramethylindane.

4. The diaminoindane derivative of claim 2 wherein the derivative is 4,7-diamino-1,1,6-trimethylindane.

5. The diaminoindane derivative of claim 2 wherein the derivative is 5,7-diamino-1,1,6-trimethylindane.

6. The diaminoindane derivative of claim 2 wherein the derivative is 4,5-diamino-1,1,6-trimethylindane.

7. The diaminoindane derivative of claim 2 wherein the derivative if 5,7-diamino-1,1,4-trimethylindane.

* * * * *

UNITED STATES PATENT AND TRADEMARK OFFICE
CERTIFICATE OF CORRECTION

PATENT NO.   : 4,987,261

DATED        : January 22, 1991

INVENTOR(S)  : Yamaguchi et al.

It is certified that error appears in the above-identified patent and that said Letters Patent is hereby corrected as shown below:

Column 10:
In claim 3, line 1, delete "12" and insert therefor --2--.

Signed and Sealed this

Eleventh Day of August, 1992

*Attest:*

DOUGLAS B. COMER

*Attesting Officer*   Acting Commissioner of Patents and Trademarks